United States Patent [19]
Fields, Jr. et al.

[11] Patent Number: 6,043,384
[45] Date of Patent: Mar. 28, 2000

[54] PREPARATION OF QUINONEIMINES FROM HYDROXYPHENYLAMINES USING HYDROGEN PEROXIDE AND A CATALYST

[75] Inventors: Donald L. Fields, Jr., Copley; Raymond Lohr, Jr., Avon; Jayant S. Lodaya, Akron, all of Ohio

[73] Assignee: Flexsys America L.P., Akron, Ohio

[21] Appl. No.: 09/272,347

[22] Filed: Mar. 19, 1999

Related U.S. Application Data

[60] Provisional application No. 60/081,281, Apr. 10, 1998.

[51] Int. Cl.$^7$ .................................................. C07C 50/04
[52] U.S. Cl. ............................................................ 552/302
[58] Field of Search ............................................... 552/302

[56] References Cited

U.S. PATENT DOCUMENTS

| | | | |
|---|---|---|---|
| 2,170,191 | 8/1939 | Fisher | 18/52 |
| 4,968,843 | 11/1990 | Cottman | 564/397 |
| 5,053,540 | 10/1991 | Cottman | 564/397 |
| 5,068,439 | 11/1991 | Cottman | 564/434 |
| 5,091,545 | 2/1992 | Parker | 552/302 |
| 5,118,807 | 6/1992 | Wheeler | 544/197 |
| 5,189,218 | 2/1993 | Desmurs et al. | 564/272 |

FOREIGN PATENT DOCUMENTS

| | | | |
|---|---|---|---|
| 0 708 080 | 4/1996 | European Pat. Off. | C07C 249/02 |
| 0 708 081 | 4/1996 | European Pat. Off. | C07C 249/02 |
| 1 267 635 | 3/1972 | United Kingdom | C09B 53/00 |

OTHER PUBLICATIONS

*Derwent Abstract*, 90–354696/47, Nov. 6, 1990.
*Derwent Abstract*, 91–305160/42, Oct. 16, 1991.
*Abstract*, 95731R, Dec. 23, 1970.
*Research Disclosure*, Process of preparing polyaniline amines, Sep. 1978.

*Primary Examiner*—Paul J. Killos
*Attorney, Agent, or Firm*—Louis A. Morris

[57] ABSTRACT

A hydroxyphenylamine compound can be converted, with high selectivity, into its corresponding quinoneimine by reacting the hydroxyphenylamine with hydrogen peroxide in the presence of a catalyst.

19 Claims, No Drawings

PREPARATION OF QUINONEIMINES FROM HYDROXYPHENYLAMINES USING HYDROGEN PEROXIDE AND A CATALYST

This application claims priority to the filing date of U.S. Provisional Application 60/081,281, filed Apr. 10, 1998.

FIELD OF THE INVENTION

This invention relates to a process for preparing a quinoneimine from a corresponding hydroxyphenylamine using hydrogen peroxide in the presence of a catalyst.

BACKGROUND OF THE INVENTION

The class of cyclic enones is well known in organic chemistry. Best known examples of cyclic enones are quinones such as, for example, the benzoquinones, naphthoquinones, anthraquinones, phenanthraquinones, and the like. 1,4-Benzoquinone is commonly referred to as quinone. Quinones are generally brightly colored compounds and have versatile applications in chemical synthesis, biological uses, as redox materials, as well as in industry. There are several review articles on the chemistry and applications of quinones including, for example, *Kirk-Othmer Encyclopedia of Chemical Technology*, Third ed., Vol. 19, pages 572–605, John Wiley & Sons, New York, 1982. The synthesis of quinones is well documented. See, for example, J. Cason, *Synthesis of Benzoquinones by oxidation, in Organic Synthesis*, Vol. IV, page 305, John Wiley & Sons, New York (1948). Quinones generally are prepared by oxidizing the appropriately disubstituted aromatic hydrocarbon derivatives, the substituents being hydroxyl or amino groups in the ortho or para positions. 1,4-Benzoquinone, for example, can be made from the oxidation of hydroquinone, p-aminophenol or p-phenylenediamine, or from quinic acid. The reagents generally used for the oxidation are dichromate/sulfuric acid mixture, ferric chloride, silver (II) oxide or ceric ammonium nitrate. In these cases, oxidation of the aminoaromatic compound is accompanied by hydrolysis to the corresponding quinone. Some processes may take several hours for completion of the reaction.

Thus, some of the prior art processes utilize a catalytic agent to achieve an acceptable reaction rate while other processes proceed without catalysts. The process according to the present invention utilizes hydrogen peroxide in the presence of a catalytic agent which provides extremely high conversion, high selectivity, and fast reaction rates to prepare the quinoneimine.

A prior art process which utilizes a catalyst in the preparation of a quinoneimine compound is disclosed by Desmurs, et al. in U.S. Pat. No. 5,189,218. The process of Desmurs, et al., which converts N-(4-hydroxyphenyl)aniline into N-phenylbenzoquinone-imine, utilizes a manganese, copper, cobalt, and/or nickel compound as a catalyst in an oxidation type reaction.

Other processes are known which use oxidizing agents to convert phenylenediamines into their corresponding quinonediimines. For example, EP 708,081 (Bernhardt et al), which describes the conversion of phenylenediamines to phenylenediimines by oxidation of the diamine in an alkali/alcoholic solution, gives a general description of such processes in its background. The EP '081 process suffers from various disadvantages including long reaction times and low yields.

An oxidation process for the catalytic oxidation of hydroxy containing aromatic compounds to form their respective quinone compounds is described by Parker in U.S. Pat. No. 5,091,545. Parker teaches the use of catalytic cobalt, a primary aliphatic amine and an alcohol to convert a hydroxy containing aromatic compound to the corresponding quinone compounds.

Additional oxidation conversion processes are described by Wheeler in U.S. Pat. No. 5,118,807, by GB1,267,635 and by Haas et al, in EP 708,080. However, the use of a hydrogen peroxide in the presence of a catalytic agent in the conversion of hydroxyphenylamine compounds to give highly selective yields of quinoneimine compounds has not heretofore been suggested.

As such, the current invention is based on the problem of providing a simple and economic process for the preparation of N-substituted-quinoneimines in high yields and with high purity.

SUMMARY OF THE INVENTION

It has been discovered that hydroxyphenylamine compounds can be converted with extremely high selectivity into the corresponding quinoneimine by reaction of the hydroxyphenylamine with hydrogen peroxide in the presence of a catalytic agent. Conditions are revealed in which nearly quantitative yields have been obtained.

In contrast to prior art, an advantage of the present invention is that the conversion of hydroxyphenylamine to the corresponding quinoneimine is nearly quantitative. Thus, very little waste material remains upon completion of the reaction.

Another advantage is that the hydrogen peroxide/catalytic agent combination, as set forth herein, provides an extremely high conversion, high selectivity and faster more complete reaction compared to prior art processes.

Still further advantages of the present invention will become apparent to those skilled in the art upon reading and understanding the following detailed description of the preferred embodiments.

DETAILED DESCRIPTION OF THE INVENTION

The object of the present invention is to provide an effective process for converting hydroxyphenylamines into their corresponding quinoneimines.

In accordance with the object of the invention, a hydroxyphenylamine (ortho or para) according to Formula Ia or Ib:

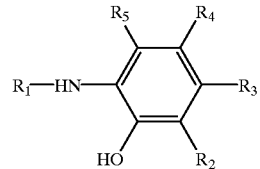

Formula Ia

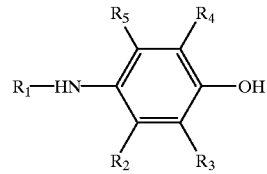

Formula Ib wherein $R_1$ is selected hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_1$ groups may be linear or branched and each of the $R_1$ groups may be further substituted where appropriate; further wherein $R_2$, $R_3$, $R_4$, and $R_5$ are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted where appropriate; is reacted with hydrogen peroxide in the presence of a catalytic agent.

The reaction produces a corresponding quinoneimine according to Formula IIa or IIb:

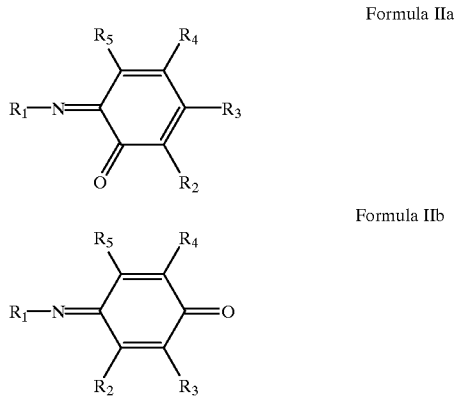

Formula IIa

Formula IIb wherein $R_1$, $R_2$, $R_3$, $R_4$, and $R_5$ are the same as in the compound according to Formula Ia or Ib.

The reaction is represented as follows:

Reaction Scheme 1

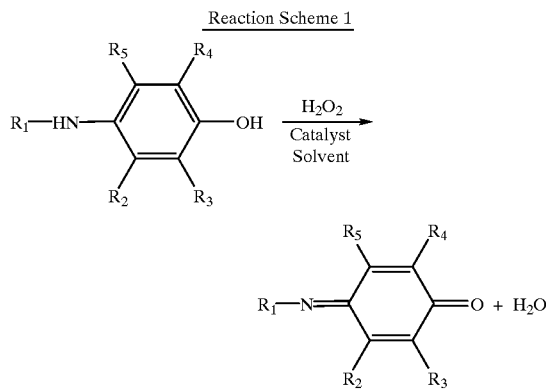

More particularly, the $R_1$ variables are selected from hydrogen, hydroxyl, C1–C50 alkyl, C1–C50 alkoxy, C6–C40 aryloxy, C2–C50 alkenyl, C3–C20 cycloalkyl, C6–C40 aryl, C7–C50 aralkyl, C7–C50 alkaryl, C1–C20 alkylamino, C6–C40 arylamino, C3–C30 heterocyclic containing one or more N, O, S, or P atoms, C1–C50 acyl, aroyl, cyano, halogen such as F, Br, I, or Cl, thiol, C1–C50 thioalkyl, C6–C40 thioaryl, amino, nitro, sulfonate having the formula $SO_3X$ wherein X is selected from sodium, C1–C50 alkyl, or C6–C40 aryl, sulfone, sulfonamide, carboxylic acid, C1–C50 alkyl ester and, C6–C40 aryl ester, wherein the alkyl moieties in the $R_1$ groups may be linear or branched and each of the $R_1$ groups may be further substituted where appropriate; further wherein $R_2$, $R_3$, $R_4$, and $R_5$ are the same or different and are selected from hydrogen, hydroxyl, C1–C50 alkyl, C1–C50 alkoxy, C6–C40 aryloxy, C2–C50 alkenyl, C3–C20 cycloalkyl, C6–C40 aryl, C7–C50 aralkyl, C7–C50 alkaryl, C1–C20 alkylamino, C,6–C40 arylamino, C3–C30 heterocyclic containing one or more N, O, S, or P atoms, C1–C50 acyl, aroyl, cyano, halogen such as F, Br, I, or Cl, thiol, C1–C50 thioalkyl, C6–C40 thioaryl, amino, nitro, sulfonate having the formula $SO_3X$ wherein X is selected from sodium, C1–C50 alkyl, or C6–C40 aryl, sulfone, sulfonamide, carboxylic acid, C1–C50 alkyl ester and, C6–C40 aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted where appropriate.

Examples of satisfactory radicals for $R_1$, $R_2$, $R_3$, $R_4$, and $R_5$ are linear or branched alkyls such as methyl, ethyl, propyl, butyl, pentyl, hexyl, heptyl, octyl, nonyl, decyl, dodecyl, and the like; aryls such as phenyl, naphthyl, anthracyl, tolyl, ethylphenyl, 1-ethyl-3-methylpentyl, 1-methylheptyl, and the like; cycloalkyls such as cyclobutyl, cyclopentyl, cyclohexyl, cyclooctyl, and the like. Other examples include allyl and isobutenyl; 1,3,5-sym-triazinyl, 2-benzothiazolyl, 2-benzimidazolyl, 2-benzoxazolyl, 2-pyridyl, 2-pyrimidinyl, 2,5-thiadiazolyl, 2-pyrazinyl, adipyl, glutaryl, succinyl, malonyl, acetyl, acrylyl, methacrylyl, caproyl, 3-mercaptopropionyl, benzoyl, phthaloyl, terephthaloyl, aminocarbonyl, carbethoxy, carbonyl, formyl, and the like. These are merely exemplary radicals and are in no way intended to limit the scope of the invention The hydrogen peroxide used in the reaction according to the present invention is typically present in an amount ranging from 1.05 to 2.05 parts per equivalent of hydroxyphenylamine. Use of less than one equivalent will tend to produce blends of quinoneimine and unreacted hydroxyphenylamine. The strength of the hydrogen peroxide can range from 5% to 85% (wt% in aqueous solution). The strength is preferably between 10% and 35%.

Catalytic agents which are used along with the hydrogen peroxide include, but are not limited to, carbon supported catalysts such as Pt/C, Cu/C and Pd/C; modified activated carbon catalysts such as those produced by removing surface oxides therefrom as set forth in U.S. Pat. No. 4,624,937, the disclosure of which is incorporated herein by reference; water soluble ionic metal catalysts; activated carbon; metal oxides, such as iron oxide ($FeO_2$), manganese oxide ($MnO_2$), and copper (II) oxide ($CuO_2$); and metals, such as silver (Ag), copper (Cu), lead (Pb), vanadium (V), chromium (Cr), nickel (Ni), manganese (Mn), iron (Fe), cobalt (Co), ruthenium (Ru), rhenium (Rh), and the like.

The catalysts of the present invention cause the conversion reaction in the process according to the present invention. Even in systems where the oxidizing agent, aqueous hydrogen peroxide, is soluble in the solvent solution of hydroxyphenylamine (i.e. acetronitrile in N,N-dimethylformamide) there is no reaction until the catalyst is added. It is advantageous to utilize solid catalysts in the reaction according to the present invention as there is ease in recovery of the solid catalysts, via filtration, and the solid catalysts can be reused in the process. There are also advantages with respect to environmental containment, and there is less likelihood that there will be contamination by the catalyst in the final isolate of quinoneimine. Further, the catalysts give high conversion and excellent selectivity.

The reaction, according to the present invention, takes place in either a homogeneous or two-phase solvent system.

Water soluble organic solvents are used for the homogeneous reaction while water insoluble organic hydrocarbon solvents yield the two-phase system. The two-phase system also includes water. The two-phase oxidation system provides ease of separation of the organic components (both quinoneimine and solvent) from the spent aqueous peroxide layer. Organic aprotic solvents useable in the process of the present invention include, but are not limited to, ketones, cyclohexanone, 4-methyl-2-pentanone (methyl isobutyl ketone), 5-methyl-2-hexanone, methyl ethyl ketone; aliphatic and aromatic hydrocarbons as such as hexanes, heptanes, toluene, xylenes, nitrites such as acetonitrile; halogenated solvents such as chloroform, dichloromethane, carbon tetrachloride; water soluble solvents such as dimethyl sulphoxide, N-methyl-2-pyrrolidone, sulfolane, dimethylformanide; esters such as ethyl acetate; ethers such as 1,4-dioxan, and mixtures thereof. The solvent(s) should be selected based on the ability of the solvent to dissolve the starting material (hydroxyphenylamine) without dissolving or solubilizing the hydrogen peroxide. Solvents in which hydrogen peroxide is soluble may proceed to cause undesirable side reactions with the quinoneimine end product.

The initial hydroxyphenylamine concentration may range in amounts of from 1% to 100% w/v. Preferably, the initial hydroxyphenylamine concentration ranges from 25% to 60% w/v.

The present reaction may take place at temperatures from −200° C. to 150° C., preferably from 25° C. to 70° C., depending on the solvent.

As mentioned above, water soluble ionic metal catalysts can also be used for the conversion reaction according to the present invention. Examples of such water soluble ionic metal catalysts include, but are not limited to, sodium tungstate ($Na_2WO_4$) and copper sulfate ($CuSO_4$. However, the use of the aforementioned water soluble ionic metal catalysts causes a potential for product contamination due to incomplete separation or product complexation with these cations. Additionally, the water soluble catalysts produce an aqueous stream containing the metal catalysts which can create environmental concerns.

A phase-transfer catalyst may be utilized to accelerate the rate of reaction with the above mentioned water soluble metal catalysts. The addition of tricaprylmethylammonium chloride (Aliquat7 336, Henkle Corp.) to the sodium tungstate/hydrogen peroxide system increases in the rate of conversion of the quinoneimine from the corresponding hydroxyphenylamine.

A phase transfer catalyst can be added directly to the reaction mixture or it can be dissolved in one of the reagents such as hydroxyphenylamine. The phase transfer catalyst may also be dissolved in a solvent used in the process or in water before addition to the reaction mass.

Another means by which the rate of reaction may be increased is by increasing the stirring or mixing rate in the reaction. By increasing the stirring or mixing, the reaction rate may be effectively adjusted to proceed at a faster pace when necessary.

The present invention can be more clearly illustrated by the following examples.

EXAMPLE 1

A solution of 2.0g. of p-anilinophenol (4-hydroxydiphenylamine) (98% Pfaltz+Bauer, Inc.) and 8.0 g. of toluene were charged to a 100 ml round-bottomed flask equipped with a dropping funnel and an efficient stirrer. A water bath was used to heat and maintain the temperature of this solution at 35EC. Catalyst (0.1052 g. of 3% Pt/C with 49.77% $H_2O$ [Johnson Matthey]) was added and hydrogen peroxide (7.7 g. of 5.0% $H_2O_2$) was metered into the flask over a 15 min. period. The mixture was allowed to stir for an additional 10 min. and filtered to remove the catalyst. The toluene layer was analyzed by HPLC. No p-anilinophenol could be detected and the quinoneimine (QI) assayed at >99.2% when normalized with the toluene peak removed from the analysis.

EXAMPLE 2

A solution of 5.0 g. of p-anilinophenol (4-hydroxydiphenylamine) (0.0265 moles) and 20.0 g. of methylene chloride were charged to a 100 ml round-bottomed flask equipped with a thermometer, dropping funnel and an efficient stirrer. Catalyst (0.1531 g. of 3%Pt/C with 49.77% $H_2O$) was added. Hydrogen peroxide (18.9 g. of 5.0% $H_2O_2$ [0.0278 moles]) was added drop wise with stirring over a 30 min. period. This addition was started at room temperature and the rate of addition was controlled to maintain the reaction temperature at 30∀1EC. The mixture was allowed to stir for an additional 10 min. after peroxide addition and filtered to remove the catalyst. This catalyst was rinsed with 5.0 g. methylene chloride. The aqueous and organic layers were separated and the quinoneimine (QI) methylene chloride layer was analyzed by HPLC (99.7% with no starting material detected).

The QI was isolated 4.95 g. by removing the methylene chloride under vacuum (rotovap). The isolated material melted at 92–96EC. The air-dried catalyst weighed 0.1177 g.

EXAMPLE 3

A solution of 40.0 g. of p-anilinophenol (4-hydroxydiphenylamine) (0.216 moles) and 60.0 g. of toluene were charged to a 250 ml round-bottomed flask equipped with a thermometer, a dropping funnel and an efficient stirrer. Catalyst (0.5016 g. of 3% Pt/C with 49.77% $H_2O$) was added. Hydrogen peroxide (15.4 g. of 50% $H_2O_2$ [0.227 moles]) was diluted to 15% by the addition of 36.0 g. of water. This peroxide was added drop wise with stirring at a rate which maintained the reaction temperature at 36∀1EC. The addition took 2 hrs. and the mixture was allowed to stir for an additional 30 min. after peroxide completion in order to cause complete conversion of the starting material to quinoneimine. The mixture was filtered to remove the catalyst and then rinsed with 10.0 g. toluene. Saturated sodium chloride (25.0 g.) was added to the above mixture and extracted. The aqueous and organic layers were separated and the QI was isolated by removing the toluene under vacuum (rotovap-water bath at 45EC). This isolated quinoneimine (QI) (40.2 g.) HPLC assayed at 98.7% QI with 0.7% p-anilinophenol. The isolated air-dried catalyst weighed 0.5206 g.

The above catalyst was recharged to another 40.0 g. of p-anilinophenol dissolved in 60.0 g. of toluene. Fresh Pt/C catalyst (0.2013 g. wet) was added and 51.4 g. of 15% hydrogen peroxide was added drop wise over a 2 hr. period. The toluene layer was sampled for HPLC analysis after this peroxide addition followed by a 30 min. hold time with stirring. The QI assayed at 99.3% with 0.6% starting material after the chromatogram was normalized to remove the toluene peak.

Quinoneimines exhibit multiple activities in vulcanized elastomers. Such activities include long term antioxidant activity. In fact, the antioxidant capacity of the quinoneimine antidegradants persists even after the vulcanizate has been extracted with solvents. In addition, quinoneimines provide the beneficial antioxidant activity without the negative effect on scorch generally associated with other antidegradants common to the industry. Quinoneimines have also been used to modify dynamic-mechanical properties of a vulcanizate. Further, the quinoneimines, and their derivatives, can be used in the preparation of other organic compounds.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the invention, it is claimed:

1. A process for preparing a quinoneimine by reacting a corresponding hydroxyphenylamine with hydrogen peroxide in the presence of a catalyst.

2. The process of claim 1 wherein the catalyst is a solid catalyst elected from palladium/carbon (Pd/C), platinum/carbon (Pt/C), copper/carbon (Cu/C), iron oxide ($FeO_2$), copper (II) oxide ($CuO_2$), manganese oxide ($MnO_2$), silver (Ag), a water soluble ionic metal catalyst, activated carbon or a modified activated carbon catalyst said modified activated carbon catalyst characterized by having surface oxides removed therefrom, copper (Cu), lead (Pb), vanadium (V), chromium (Cr), nickel (Ni), manganese (Mn), iron (Fe), cobalt (Co), ruthenium (Ru), and rhenium (Rh).

3. The process of claim 1 wherein the hydroxyphenylamine is an ortho- or para-hydroxyphenylamine of the following Formula Ia or Ib:

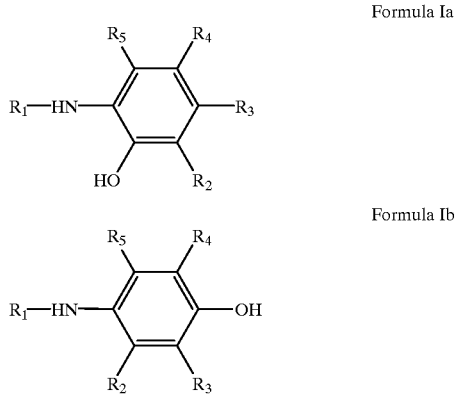

Formula Ia

Formula Ib wherein $R_1$ is hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_1$ groups may be linear or branched and each of the $R_1$ groups may be further substituted; further wherein $R_2$, $R_3$, $R_4$, and $R_5$ are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted and

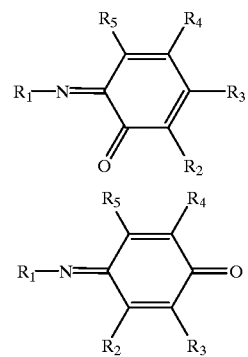

further wherein the resulting corresponding quinoneimine is of the following Formula IIa or IIb:

Formula IIa Formula IIb wherein $R_1$, $R_2$, $R_3$, $R_4$, and $R_5$ are the same as in the compound of Formula I.

4. The process of claim 3 wherein $R_1$=phenyl, naphthyl or anthracyl.

5. The process of claim 3 wherein $R_1$=phenyl, $R_2$=hydrogen, $R_3$=hydrogen, $R_4$=hydrogen and, $R_5$=hydrogen.

6. The process of claim 3 wherein the hydroxyphenylamine is a para-hydroxyphglamine.

7. The process of claim 1 wherein the reaction takes place in the presence of a solvent system selected from a homogeneous or a two-phase solvent system.

8. The process of claim 7 wherein the solvent is a two phase solvent system comprising a water insoluble organic solvent in combination with water.

9. The process of claim 7 wherein the solvent system is a homogeneous solvent system comprising one or more water soluble organic solvents.

10. The process of claim 8 wherein the water insoluble organic solvent is selected from toluene and methyl chloride.

11. The process of claim 1 wherein the reaction takes place at a temperature of between 25° C. and 70° C.

12. The process of claim 1 wherein the hydrogen peroxide is present in an amount ranging from about 1.05 to about 2.05 parts per equivalent of hydroxyphenylamine.

13. The process of claim 1 wherein the strength of the hydrogen peroxide is between 10% and 35% (wt % aqueous solution).

14. A process for preparing a quinoneimine by reacting the corresponding hydroxyphenylamine with hydrogen peroxide in the presence of a catalyst wherein the hydroxyphenylamine is an ortho- or para-hydroxyphenylamine of the following Formula Ia or Ib:

Formula Ia

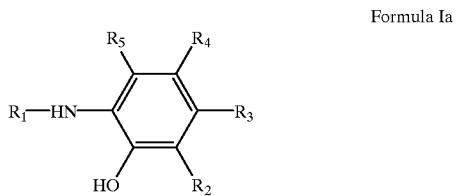

Formula Ib

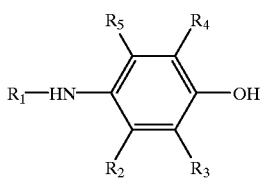

wherein $R_1$ is hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_1$ groups may be linear or branched and each of the $R_1$ groups may be further substituted; further wherein $R_2$, $R_3$, $R_4$, and $R_5$ are the same or different and are selected from hydrogen, hydroxyl, alkyl, alkoxy, aryloxy, alkenyl, cycloalkyl, aryl, aralkyl, alkaryl, alkylamino, arylamino, heterocycle, acyl, aroyl, cyano, halogen, thiol, thioalkyl, thioaryl, amino, nitro, sulfonate, sulfone, sulfonamide, carboxylic acid, alkyl ester and, aryl ester, wherein the alkyl moieties in the $R_2$, $R_3$, $R_4$, and $R_5$ groups may be linear or branched and each of the $R_2$, $R_3$, $R_4$, and $R_5$ groups may be further substituted and further wherein the resulting corresponding quinoneimine is of the following Formula IIa or IIb:

Formula IIa

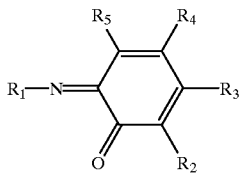

Formula IIb

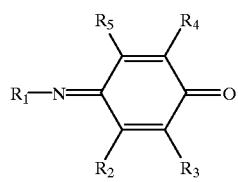

wherein $R_1$, $R_2$, $R_3$, $R_4$, and $R_5$ are the same as in the compound of Formula Ia or Ib wherein the reaction takes place in a homogenous solvent system or in a two-phase solvent system comprising a water insoluble organic solvent and water.

15. The process of claim 14 wherein the homogeneous solvent is selected water soluble organic solvents.

16. The process of claim 14 wherein the water insoluble organic solvent of the two phase solvent system is selected from toluene and methyl chloride.

17. The process of claim 14 wherein the catalyst is a solid catalyst selected from palladium/carbon (Pd/C), platinum/carbon (Pt/C), copper/carbon (Cu/C), iron oxide (FeO$_2$), copper (II) oxide (CuO$_2$), manganese oxide (MnO$_2$), silver (Ag), a water soluble ionic metal catalyst, activated carbon or a modified activated carbon catalyst said modified activated carbon catalyst characterized by having surface oxides removed therefrom, copper (Cu), lead (Pb), vanadium (V), chromium (Cr), nickel (Ni), manganese (Mn), iron (Fe), cobalt (Co), ruthenium (Ru), and rhenium (Rh).

18. The process of claim 14 wherein $R_1$=phenyl, naphthyl, or anthracyl.

19. The process of claim 14 wherein the compound of Formula I is 4-hydroxy-diphenylamine.

* * * * *

UNITED STATES PATENT AND TRADEMARK OFFICE
CERTIFICATE OF CORRECTION

PATENT NO. : 6,043,384
DATED : March 28, 2000
INVENTOR(S) : Donald L. Fields, Jr., Raymond Lohr, Jr., Jayant S. Lodaya It is certified that error appears in the above-identified patent and that said Letters Patent is hereby corrected as shown below:

Column 8,
Line 1, please insert "Formula IIa" on the top right of the first formula and "formula IIb" on the top right of the second formula.
Line 17-18, please delete "further wherein the resulting corresponding quinoneimine is of the following Formula IIa or IIb: " and insert it in column 8 line 1-2.
Line 20, please delete "Formula IIa Formula IIb."

Signed and Sealed this

Nineteenth Day of June, 2001

Attest:

NICHOLAS P. GODICI
Attesting Officer   Acting Director of the United States Patent and Trademark Office